(12) United States Patent
Gliner et al.

(10) Patent No.: US 9,970,813 B1
(45) Date of Patent: May 15, 2018

(54) UV DETECTION OF STERILANT CONCENTRATION AND DISSIPATION IN A VOLUME OF A CHAMBER

(71) Applicant: Biosense Webster (Israel) Ltd., Yokneam (IL)

(72) Inventors: Vadim Gliner, Haifa (IL); Assaf Govari, Haifa (IL); Yaron Ephrath, Karkur (IL); Andres Claudio Altmann, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 0 days. days.

(21) Appl. No.: 15/704,075

(22) Filed: Sep. 14, 2017

(51) Int. Cl.
| | |
|---|---|
| *G01J 1/42* | (2006.01) |
| *A61L 2/28* | (2006.01) |
| *A61L 2/20* | (2006.01) |
| *C02F 1/32* | (2006.01) |
| *H05B 3/00* | (2006.01) |
| *B01J 19/12* | (2006.01) |

(52) U.S. Cl.
CPC ............... *G01J 1/429* (2013.01); *A61L 2/208* (2013.01); *A61L 2/28* (2013.01); *B01J 19/123* (2013.01); *C02F 1/32* (2013.01); *H05B 3/0052* (2013.01)

(58) Field of Classification Search
CPC .......... A61L 2/208; A61L 2/28; B01J 19/123; C02F 1/32; G01J 1/429; H05B 3/0052
See application file for complete search history.

(56) References Cited

U.S. PATENT DOCUMENTS

| | | | |
|---|---|---|---|
| 6,269,680 B1 | 8/2001 | Prieve et al. | |
| 6,333,002 B1* | 12/2001 | Jacobs | A61L 2/208 422/3 |
| 2006/0222576 A1 | 10/2006 | Rudkowski et al. | |
| 2010/0053621 A1* | 3/2010 | Olson | A61L 2/208 356/437 |
| 2015/0374868 A1 | 12/2015 | Bruce et al. | |

OTHER PUBLICATIONS

Han, De-Man, et. al., Poly (N-isopropylacrylamide)-co-(acrylic acid) microgel/Ag nanoparticle hybrids for the colorimetric sensing of H2O2, Nanoscale, 2015, 7, 2784-2789.

* cited by examiner

*Primary Examiner* — Mark R Gaworecki
(74) *Attorney, Agent, or Firm* — Volpe and Koenig, P.C.

(57) ABSTRACT

A method and system for UV detection of sterilant concentration and dissipation in a volume of a chamber may comprise focusing cameras on at least one point of an object in the chamber; transmitting UV light and sterilant into the chamber; scanning, using the cameras, the at least one point of the object and determining an amount of absorbance at the points; calculating, using the amount of absorbance, a concentration of the sterilant for each of the one or more points; and when the concentration is greater than a threshold, removing the sterilant from the volume. The sterilant may be hydrogen peroxide. The cameras may be stereoscopic cameras. The chamber may be partitioned into a grid of voxels for scanning.

20 Claims, 6 Drawing Sheets

UV DETECTION OF STERILANT CONCENTRATION AND DISSIPATION IN A VOLUME OF A CHAMBER

SUMMARY

Methods and apparatus for ultraviolet ("UV") detection of a sterilant, such as hydrogen peroxide ("H2O2"), concentration and dissipation in a volume, such as cameras or the like, are provided.

A method for UV detection of sterilant concentration and dissipation in a volume may comprise focusing cameras on at least one point of an object in the volume; transmitting UV light and sterilant into the volume; scanning, using the cameras, the at least one point of the object and determining an amount of absorbance at the at least one point; calculating, from said determined amount of absorbance, a concentration of the sterilant for each of the at least one point; and, when the concentration is greater than a threshold, removing the sterilant from the volume.

In one embodiment of the method, the step of scanning further comprising partitioning the chamber into a grid of voxels and scanning the voxels. In one embodiment, the step of calculating being performed by measuring the amount of absorbance at the at least one point. In one embodiment, the amount of absorbance is proportional to the concentration of the sterilant. In one embodiment, the sterilant is hydrogen peroxide. In one embodiment, the threshold is 630 mg/L. In one embodiment, the cameras are stereoscopic cameras.

A system for UV detection of sterilant concentration and dissipation in a volume of a chamber may comprise two or more cameras; a volume of a chamber; an object; and a processor which is configured to focus the cameras on at least one point of the object in the volume of the chamber; transmit UV light and sterilant into the volume; scan, using the cameras, the at least one point of the object and determine an amount of absorbance at the at least one point; calculate, from said determined amount of absorbance, a concentration of the sterilant for each of the at least one point; and when the concentration is greater than a threshold, remove the sterilant from the volume.

In one embodiment, the processor is further configured to partition the chamber into a grid of voxels and scan the voxels. In one embodiment, the processor is further configured to perform the calculation by measuring the amount of absorbance at the at least one point. In one embodiment, the amount of absorbance is proportional to the concentration of the sterilant. In one embodiment, the sterilant is hydrogen peroxide. In one embodiment, the threshold is 630 mg/L. In one embodiment, the cameras are stereoscopic cameras.

A computer program product for UV detection of sterilant concentration and dissipation in a volume is also presented.

These and other objects, features and advantages of the present invention will be apparent from the following detailed description of illustrative embodiments thereof, which is to be read in connection with the accompanying drawings.

BRIEF DESCRIPTION OF THE DRAWINGS

The present invention is illustrated by way of example, and not by way of limitation, in the figures of the accompanying drawings in which.

DETAILED DESCRIPTION

Figure 1:
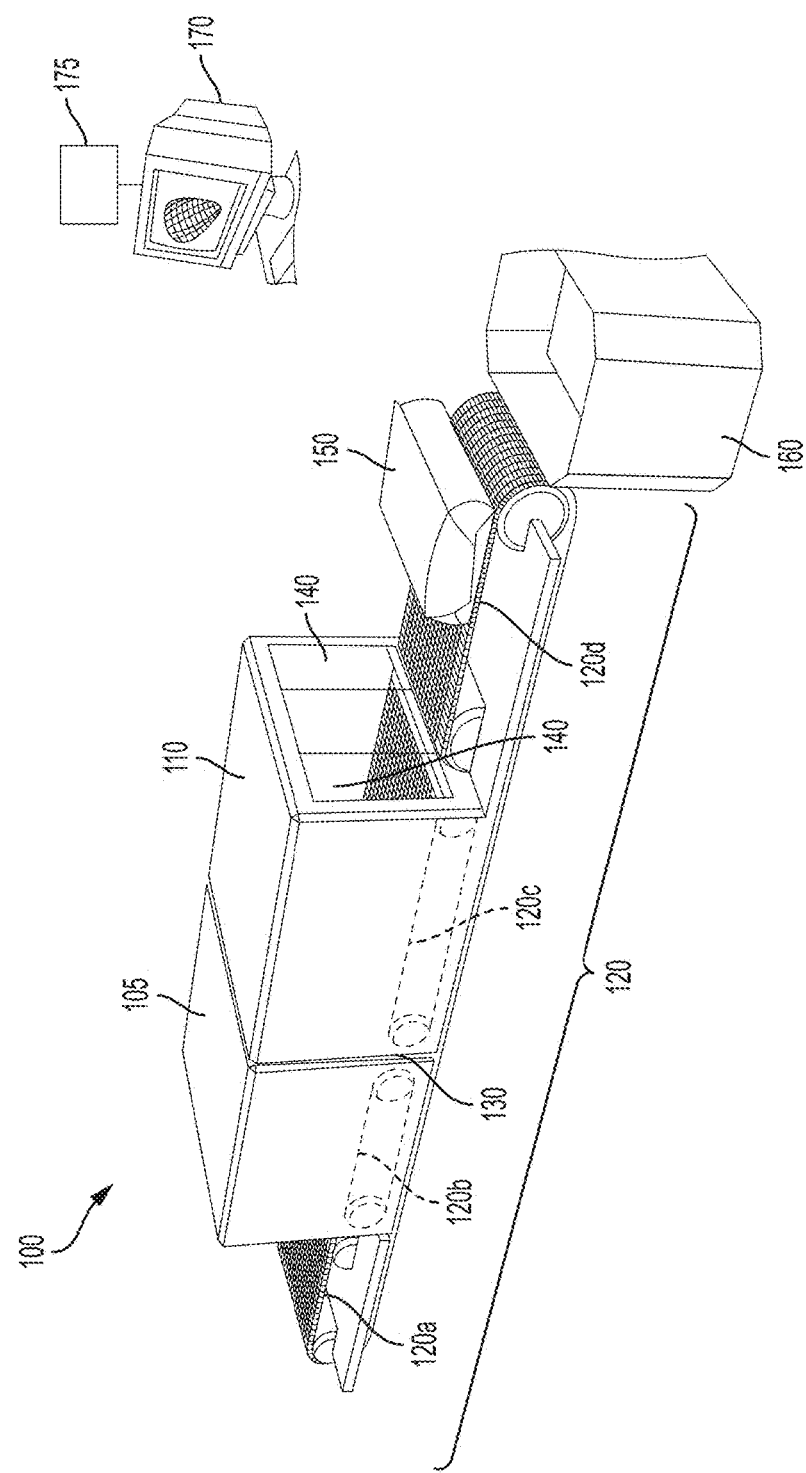
FIG. 1 is an illustration of an embodiment according to the invention showing cleansed and packaged instruments exiting from a cleansing and packaging apparatus.

The present invention is directed to methods and apparatus related to UV detection of sterilant concentration and dissipation in a volume, using stereoscopic cameras or the like.

One of the standard methods for low temperature sterilization of medical equipment is to use a combination of a sterilant such as hydrogen peroxide vapor with a low temperature plasma in a sterilization chamber. During the course of the sterilization process, the hydrogen peroxide concentration is measured as it is consumed, and hydrogen peroxide is added, as necessary, to the chamber to maintain the concentration at a satisfactory level. A present method for measuring the hydrogen peroxide concentration uses an ultraviolet light source transmitted through the chamber, and the received ultraviolet light is measured with a single ultraviolet light detector that is located far from the source. The level of the received ultraviolet light is used to calculate a gross hydrogen peroxide concentration reading.

In current plasma sterilization systems using hydrogen peroxide gas plasma technology, a problem occurs because it is not possible to determine how much the hydrogen peroxide vapor has spread within the vacuum chamber. Accordingly, uniform dissipation and distribution of the hydrogen peroxide is uncertain. Existing systems feature only one biological sensor (to detect sterilization) inside the system, amid all the trays that are filled with objects, such as medical instruments, and covered with drapes.

In practice, concentration of a sterilant such as hydrogen peroxide may vary greatly within the chamber, especially when sterilizing equipment with narrow lumens, such as catheters, endoscopes, etc., restrict diffusion of sterilant vapor. There may be areas of the chamber which are exposed to higher or lower concentrations of hydrogen peroxide due to such flow restrictions. Thus the gross reading referred to above may not give an accurate picture of the concentration distribution over the entire chamber.

Therefore, an improved plasma sterilization system that allows the user to confirm that the vapor has spread through the entire volume of the chamber to reach all necessary points to accomplish sterilization is needed.

The inventive plasma sterilization system described herein provides for the visualizing of the sterilant, e.g., hydrogen peroxide vapors, spreading inside the chamber in three dimensions ("3D") using stereoscopic UV cameras in the chamber. This visualizing may be, for example, a mapping of the hydrogen peroxide vapor concentration over the entire chamber and/or over the entire surface of one or more medical instruments being steralized. This process can be used to determine at least the following information: the approximate concentration of the vapor in one or a plurality of locations throughout the chamber, where the vapor spread, whether it came into contact with the objects, how long it lasted in the chamber, and other parameters. Further, the inventive system can be used to eliminate the biological indicator sensor used in existing systems.

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

FIG. 1 depicts example cleansing and packaging system 100 that provides an improved sanitation, sterilization and packaging process for objects such as surgical instruments or the like and eliminates the potential for contamination due to exposure to microbial elements in unsealed conditions. For example, U.S. patent application Ser. No. 15/602,739 to Altmann et al., incorporated herein by reference, discloses an example cleansing and packaging system. As shown in FIG. 1, the cleansing and packaging system 100 has a sealable cleansing compartment or chamber 105 and a sealable packaging compartment 110. The cleansing compartment 105 and the packaging compartment 110 are preferably joined contiguously to each other as shown in the example cleansing and packaging system 100, but may be disposed serially without being physically connected. In the depicted example, the cleansing compartment 105 includes both a sanitation system and a sterilization system and the packaging compartment 110 includes a packaging system. Of course, in another embodiment, the cleansing compartment 105 may just include a sterilization system in conjunction with the packaging system of the packaging compartment 110.

In addition, the example cleansing and packaging system 100 has a conveyor system 120 partially encased by and configured to transport items through the compartments 105 and 110. As illustrated in FIG. 1, the conveyor system 120 has four individual conveyor sections, 120a, 120b, 120c and 120d. Although the conveyor system 120 has been illustrated with these four individual conveyor sections 120a, 120b, 120c and 120d, it is understood that other embodiments of the cleansing and packaging system 100 may utilize one, single conveyor section or any other number of individual conveyor sections. Referring to FIG. 1, in general, the conveyor system 120 enters the cleansing compartment 105, runs first through the cleansing compartment 105, then through the packaging compartment 110, and then finally out of the packaging compartment 110. In particular, conveyor section 120a resides outside the entrance of the cleansing compartment 105, conveyor section 120b is encased by and configured to transport items through the cleansing compartment 105, conveyor section 120c is encased by and configured to transport items through the packaging compartment 110, and conveyor section 120d resides outside the exit of the packaging compartment 110. Thus, conveyor section 120a is configured to convey an instrument to the entrance of the cleansing compartment 105, where conveyor section 120b is configured to receive the instrument from conveyor section 120a. Conveyor section 120b is further configured to convey the instrument through the cleansing compartment 105 to the exit of the cleansing compartment 105 and entrance of the packaging compartment 110. It follows that conveyor section 120c is configured to receive the instrument from conveyor section 120b. Conveyor section 120c is further configured to convey the instrument through the packaging compartment 110 to the exit of the packaging compartment 110. Finally, conveyor section 120d is configured to receive a wrapped packaged 150 from conveyor section 120c and convey the wrapped package 150 out of the packaging compartment 110 to a container 160.

Further, the example cleansing and packaging system 100 features three sets of sealing doors. A first set of sealing doors is configured at the entry of the cleansing compartment 105 to provide a sealing entry door component (not shown). A second set of sealing doors is configured between the cleansing compartment 105 and the packaging compartment 110 to provide a sealing joining door component 130. A third set of sealing doors is configured at the exit of the packaging compartment 110 to provide a sealing exit door component 140. For each of the three aforementioned sets of sealing doors, the sealing aspect can include one or both of a liquid seal and an air-tight seal. The three sets of sealing doors may be made of a transparent material that provides for vision into the cleansing compartment 105 and the packaging compartment 110 when the three sets of sealing doors are closed. While the three sets of sealing doors may be made of a transparent material, it is not necessary for them to be made of such transparent material.

As aforementioned, while the conveyor system 120 of FIG. 1 has been illustrated with four individual conveyor sections 120a, 120b, 120c and 120d, it is understood that other embodiments of the cleansing and packaging system 100 may utilize one, single conveyor section or any other number of conveyor sections. In an alternative embodiment with one, single conveyor section running through the entire cleansing and packaging system 100, the conveyor 120 is preferably made of a substance, such as rubber, that enables the sets of sealing doors 130, 140 to sealingly engage the conveyor 120 when the sealing doors are closed. In particular, the conveyor 120 can have grooves with gaskets that provide for a vacuum seal when engaged by the sealing doors. Depending on the level and method of sterilization, the doors can, in another embodiment, be heavy drapes that prevent air movement. Such heavy drapes can be disposed at the entry of the cleansing compartment 105, between the cleansing compartment 105 and the packaging compartment 110, and at the exit of the packaging compartment 110.

The conveyor system 120 may include a controller 170 and a monitor or display screen 175. The controller 170 may send signals to and receive signals from the conveyor system 120. In one embodiment, the controller 170 may receive signals for display on the monitor 175, as is discussed in more detail with respect to FIG. 4 (below).

Figure 2:
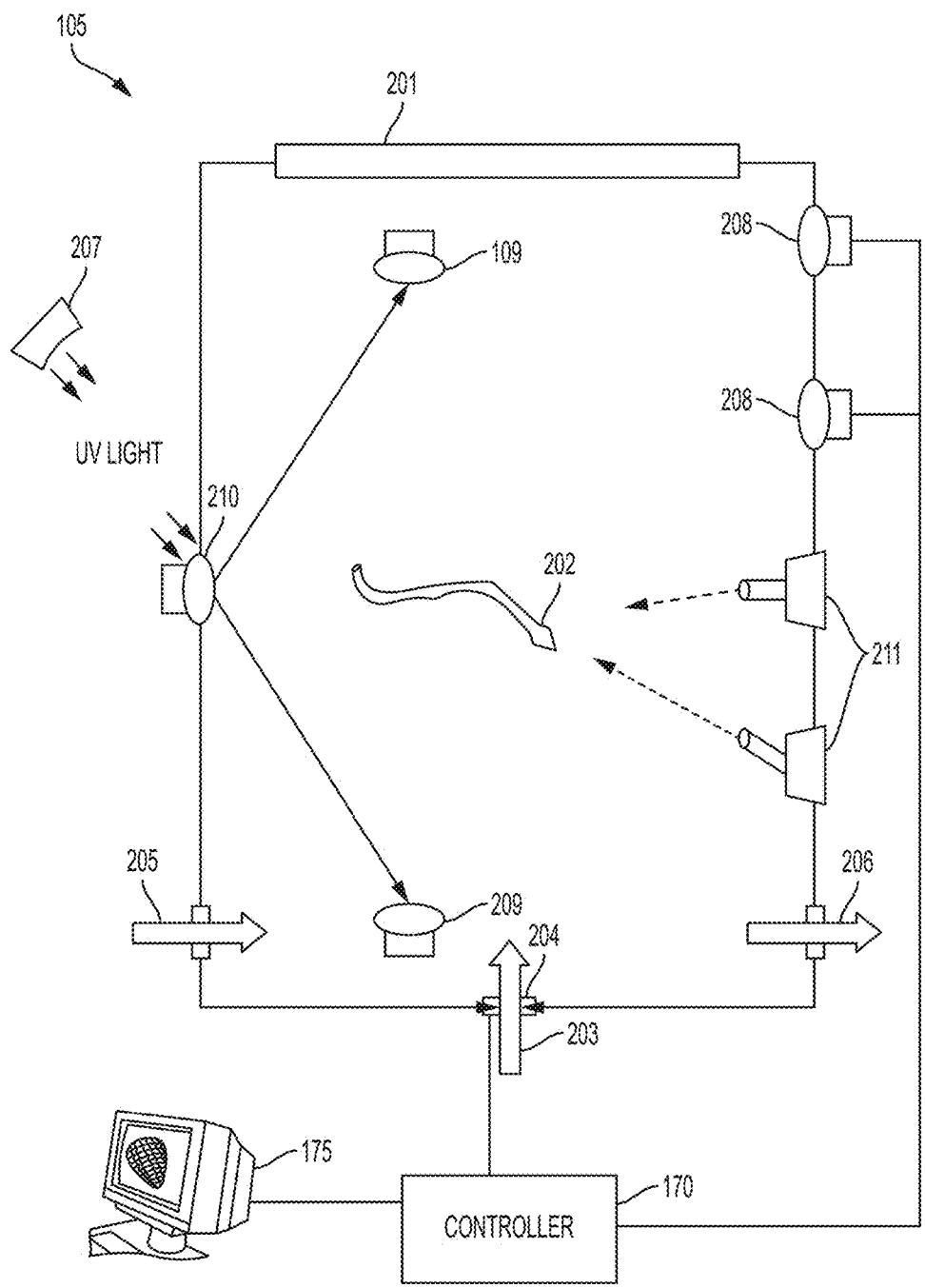
FIG. 2 is a schematic diagram of a sterilization chamber in accordance with an embodiment of the invention.

FIG. 2 is a schematic diagram of the cleansing and sterilization compartment or chamber 105 in accordance with an embodiment of the invention. The chamber 105 has a sealed portal 201 for passage of objects 202 to be sterilized, which can be assorted surgical instruments and the like. Hydrogen peroxide is admitted into the chamber 105 via an inlet 203 having a regulator or valve 204. At least one portal 205 is provided for admission of air, and gas exits from the chamber through at least one other portal 206. The chamber 105 is maintained at lower than atmospheric pressure, typically 0.5 torr, and features an ultraviolet (UV) light source 207 that transmits UV light through the chamber, which is received in multiple mural UV light detectors 208 and interior UV light detectors 209. Optics 210, having appropriate UV lenses that are associated with the UV source 207 are configured to illuminate all the detectors 208, 209. The distribution of the detectors 208, 209 in FIG. 2 is by way of example and not of limitation. The detectors 208, 209 may be distributed in the chamber such that the measurements optimally reflect the concentrations of hydrogen peroxide at the objects being sterilized. Therefore, they may be placed evenly throughout the chamber. The detectors need not be distributed in any particular order, and may even be widely scattered about and within the chamber, facing in different directions.

Also in the chamber, there are two stereoscopic cameras 211 which are constantly focused on the object 202. These stereoscopic cameras 211 view the object 202 in the three dimensional (3D) volume. More than two stereoscopic cameras can be used.

The UV light source 207 receives command signals from a controller 170 and readouts from the detectors 208, 209 as well as from the cameras 211. The valve 204 is adjusted by the controller 170 responsively to the readouts. The valve 204 regulates the inflow of hydrogen peroxide to achieve a desired optimum level (typically 95% concentration) of hydrogen peroxide within the chamber 105. Once the optimum level is achieved, in some embodiments the inflow may be discontinued and the chamber maintained in a static condition.

In one embodiment, the sterilization chamber may be made from a transparent substance, such as quartz. The hydrogen peroxide vapor absorbs UV light at high frequencies, so the two (or more) stereoscopic cameras 211 can measure the vapors in the chamber to determine the adequacy of the sterilization procedure. The vapor concentration may be measured as follows. Assume that absorbance for each wavelength is dependent on concentration, and that absorbance plus transmittance equals one (1). Accordingly, if the chamber is illuminated from one side and the camera is positioned at the other side, the transmittance of UV light can be measured based on the brightness of the pixels. The pixel is brighter as more light is transmitted, and less is absorbed.

Figure 3:
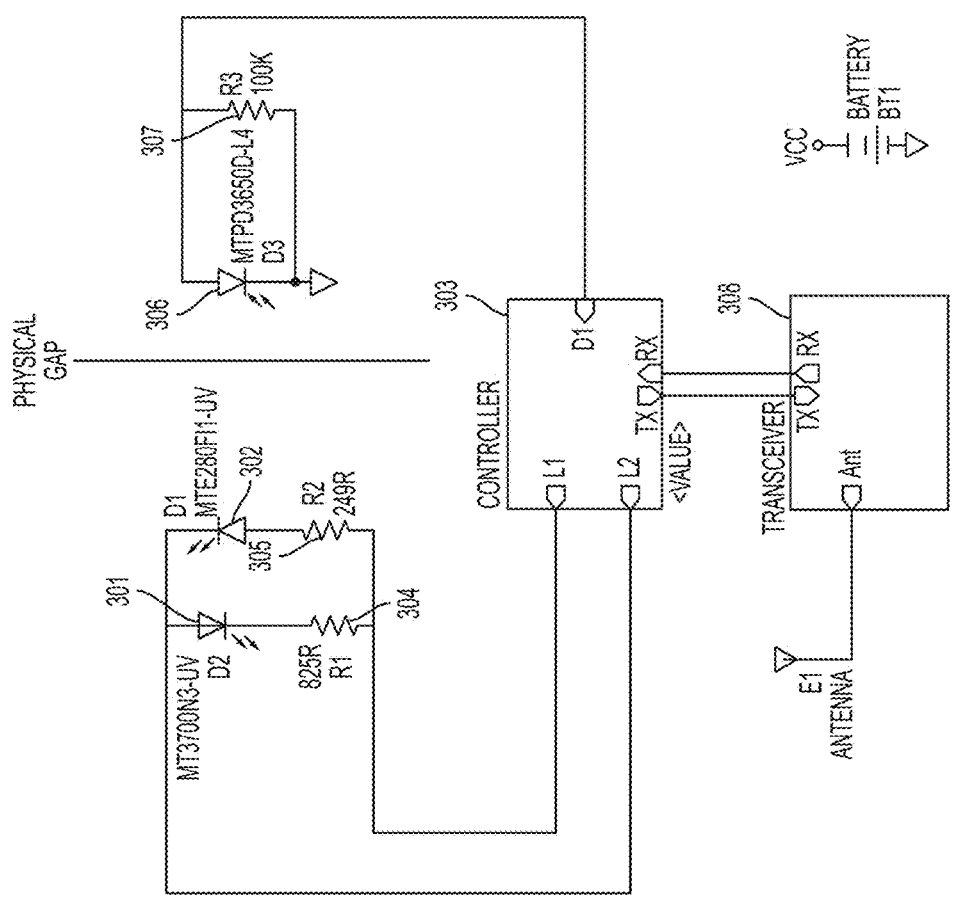
FIG. 3 is a schematic of components of the chamber shown in FIG. 1 in accordance with an embodiment of the invention.

FIG. 3 is a schematic of electrical components of the system 100 in accordance with an embodiment of the invention. In this embodiment, UV source 207 is realized as two light emitting diodes 301, 302 in parallel, both supplied by a controller 303. In another embodiment, the UV source 207 may be a UV lamp instead of diodes. The diodes 301, 302 are in series with resistors 304, 305 and emit at 280 nm and 370 nm respectively. The diodes 301, 302 may emit simultaneously at respective frequencies, or at different time intervals at the same frequency. The Goertzel algorithm may be used in detecting the signals from the diodes 301, 302. Techniques of dual wavelength ultraviolet spectroscopy are known, for example, from U.S. Pat. No. 6,269,680, which is herein incorporated by reference. In the circuitry shown in FIG. 3, diode 302 acts as a reference to compensate for internal variations in the circuitry, while diode 301 emits at a wavelength that is strongly absorbed by hydrogen peroxide vapor.

A number of other ultraviolet emitters known in the art could be used for the UV light source 207, for example, cylindrical low pressure mercury UV emitters with a spectral peak at about 254 nm. Such emitters are proposed in U.S. Patent Application Publication No. 2006/0222576, which is herein incorporated by reference. Other examples of such light sources include low pressure mercury vapor lamps, deuterium lamps, xenon lamps, light-emitting diodes and laser diodes. In general all of these are less convenient or more expensive than the dual light emitting diode configuration described above.

The detectors 208, 209 may be realized as a charge-coupled detector 306 across a resistor 307. Signals from the detector 306 are received in the controller 303 and conveyed to a remote site, such as a processor (not shown) by transceiver 308, where signal processing techniques are applied, including analog-to-digital conversion, and Fourier analysis, including the above-noted Goertzel algorithm.

Figure 4A:
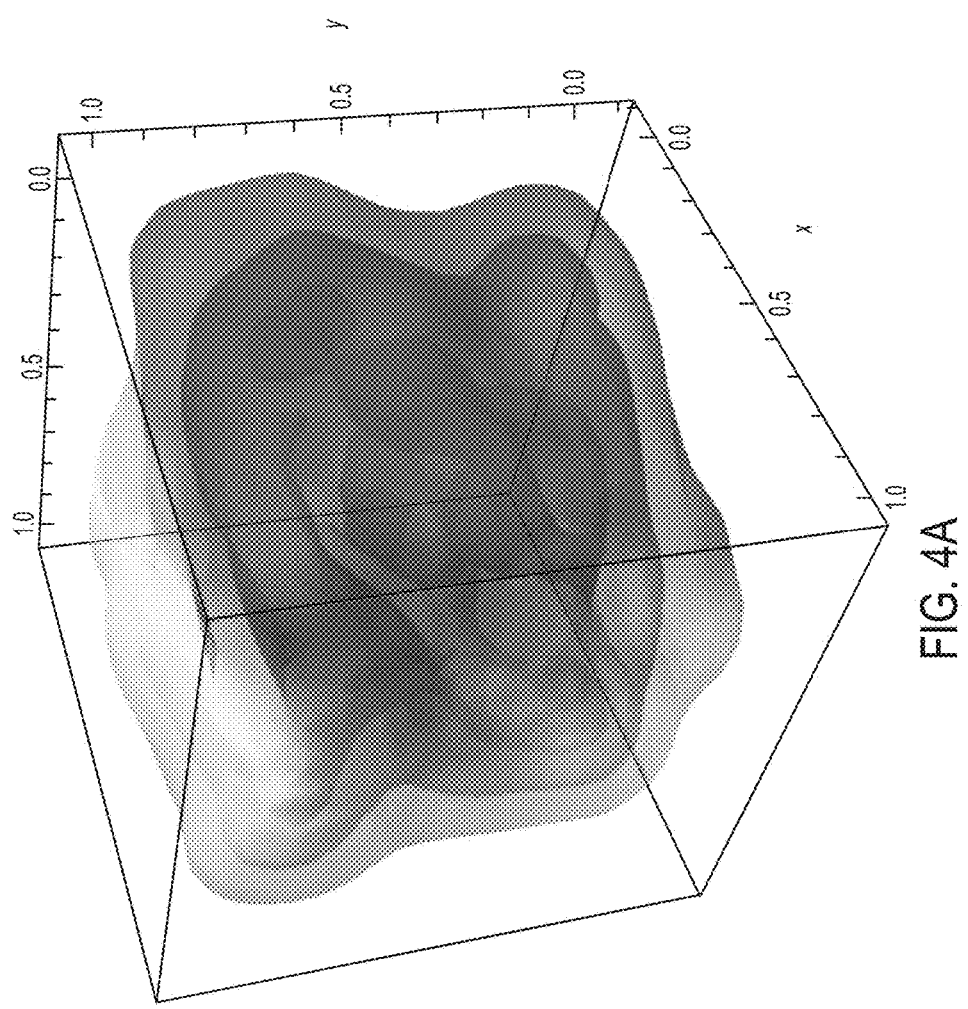
FIGS. 4A and 4B are example displays in accordance with embodiments of the invention; ands
Figure 4B:
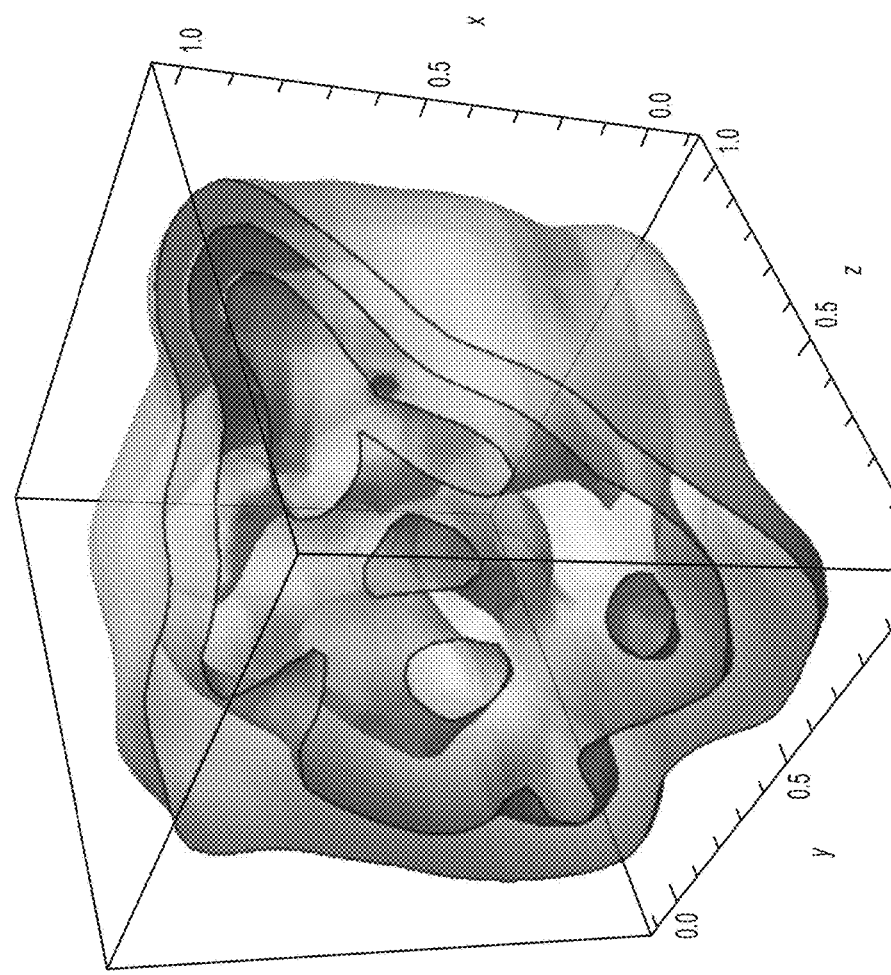

FIGS. 4A and 4B are example displays in accordance with embodiments of the present invention. The controller 170 sends and receives data 401 from one or more components of the conveyor system 120. In an embodiment shown in FIG. 4A, the data 401 may be displayed on the display monitor 175 as in which different colors or hues indicate the density of the sterilant. In an embodiment shown in FIG. 4B, the data 401 may be displayed with colors or greyscale indicating the density and density changes are emphasized by outlining. The data 401 may be displayed in color, in greyscale and/or using numerals.

Figure 5:
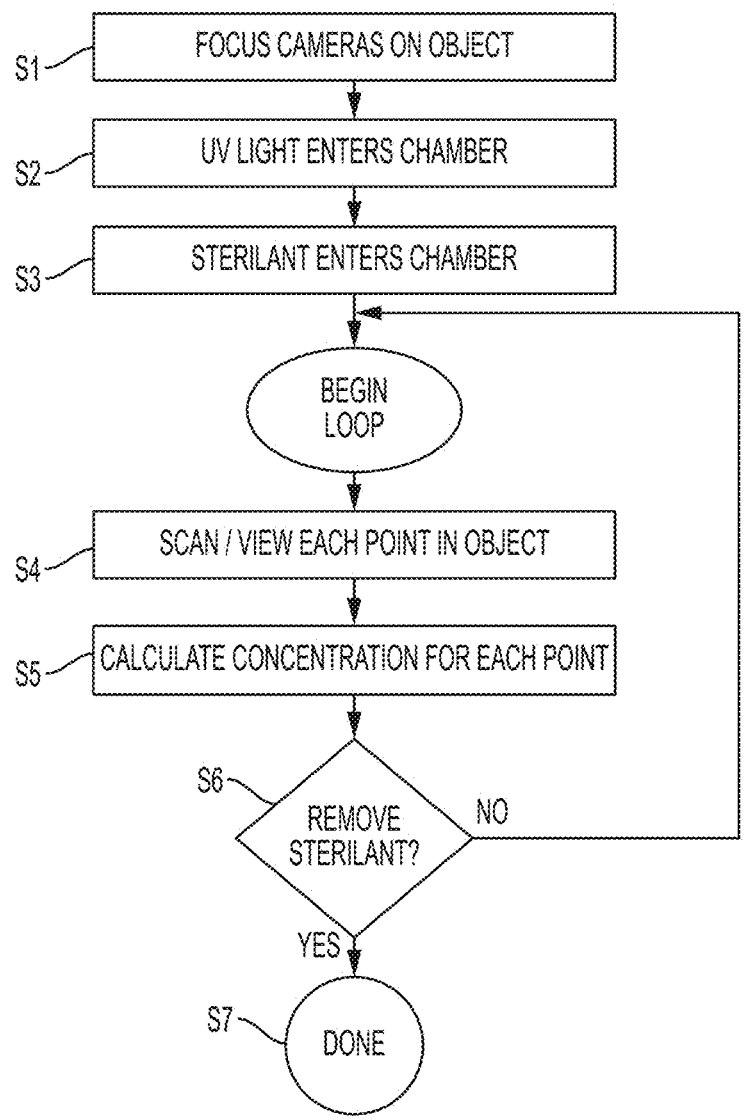
FIG. 5 is a flow diagram of an example sterilization operation that is used in conjunction with one or more disclosed embodiments.

FIG. 5 is a flow diagram of the inventive method in one embodiment. In step S1, the stereoscopic cameras 211 focus on the object 202 in the volume of the chamber 105 and the chamber volume is divided or partitioned into a grid of voxels. A typical voxel may be 1 mm×1 mm×1 mm.

In step S2, the UV light source is turned on and UV light enters the chamber 105. During step S2, every point or pixel in the chamber 105 will absorb some of the radiation from the UV light source and will transmit the non-absorbed portion.

In step S3, the sterilant enters the chamber 105. The amount of UV light received at each camera 211 increases as the sterilant enters into the chamber 105. The amount of light increases proportionally to the amount of sterilant at each point. For example, when the amount of sterilant at a particular point doubles, the amount of UV light at that point also doubles.

Next, a looping process of scanning the chamber begins. In step S4, the cameras 211 which had been focused on the object 202 and scan the grid of voxels, which includes the points on the object 202, in the chamber 105. That is, the cameras measure the amount of UV light on each point (pixel) of each voxel in the chamber 105. Note that the object 202 may exist in one or more voxels in the grid of voxels.

In step S5, the concentration of H2O2 is calculated using the amount of absorbance determined from the camera measurement of step S4. The amount of absorbance is proportional to the concentration of H2O2, so that the concentration can be calculated from the measurement of absorbance.

As described above, the amount of UV light at each point is proportional to the amount of sterilant at each point. At step S6, for each point, determine whether the concentration of sterilant exceeds a threshold. When the concentration of sterilant exceeds a threshold (S6=YES) for all of the points, then the object is successfully sterilized. In step S7, when the concentration of sterilant exceeds the threshold (S6=YES), the procedure is complete and the sterilant is removed from the chamber. In one embodiment, an ethylene oxide process is typically run at 55 degrees Celsius with a gas phase concentration of 630 mg/L. Accordingly, in one embodiment, the threshold of sterilant concentration may be 630 mg/L, so that when the sterilant concentration is 630 mg/L or more, the removal process is performed (e.g., the sterilant is removed from the chamber).

When the concentration of sterilant does not exceed the threshold (S6=NO), continue the scan at step S4.

It will be appreciated by persons skilled in the art that the present teachings are not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

It should be understood that the cleansing compartment 105 may feature any number and any combination of inspection devices, such as lights 305 and sensors 315. For both the sanitation and sterilization processes within the cleansing compartment 105, the plurality of inspection devices assists in the cleansing process for medical instruments. It is understood that the plurality of inspection devices may include a broad variety of sensors and inspection mechanisms, such as UV sensors, heat seeking detectors, biological indicators, chemical reagents, and humidity detectors.

The methods provided include implementation in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements methods described herein.

The methods or flow charts provided herein can be implemented in a computer program, software, or firmware incorporated in a non-transitory computer-readable storage medium for execution by a general purpose computer or a processor. Examples of non-transitory computer-readable storage mediums include a ROM, a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A method for UV detection of sterilant concentration and dissipation in a volume, comprising:
   focusing cameras on at least one point of an object in the volume;
   transmitting UV light and sterilant into the volume;
   scanning, using the cameras, the at least one point of the object and determining an amount of absorbance at the at least one point;
   calculating, from said determined amount of absorbance, a concentration of the sterilant for each of the at least one point; and, when the concentration is greater than a threshold, removing the sterilant from the volume.

2. The method according to claim 1, the step of scanning further comprising partitioning the chamber into a grid of voxels and scanning the voxels.

3. The method according to claim 1, the step of calculating being performed by measuring the amount of absorbance at the at least one point.

4. The method according to claim 1, wherein the amount of absorbance is proportional to the concentration of the sterilant.

5. The method according to claim 1, wherein the sterilant is hydrogen peroxide.

6. The method according to claim 1, wherein the threshold is 630 mg/L.

7. The method according to claim 1, wherein the cameras are stereoscopic cameras.

8. A system for UV detection of sterilant concentration and dissipation in a volume of a chamber, comprising:
   two or more cameras;
   a volume of a chamber;
   an object; and
   a processor which is configured to:
      focus the cameras on at least one point of the object in the volume of the chamber;
      transmit UV light and sterilant into the volume;
      scan, using the cameras, the at least one point of the object and determine an amount of absorbance at the at least one point;
      calculate, from said determined amount of absorbance, a concentration of the sterilant for each of the at least one point; and
      when the concentration is greater than a threshold, remove the sterilant from the volume.

9. The system according to claim 8, the processor further configured to partition the chamber into a grid of voxels and scan the voxels.

10. The system according to claim 8, the processor further configured to perform the calculate by measuring the amount of absorbance at the at least one point.

11. The system according to claim 8, wherein the amount of absorbance is proportional to the concentration of the sterilant.

12. The system according to claim 8, wherein the sterilant is hydrogen peroxide.

13. The system according to claim 8, wherein the threshold is 630 mg/L.

14. The system according to claim 8, wherein the cameras are stereoscopic cameras.

15. A computer software product for UV detection of sterilant concentration and dissipation in a volume of a chamber, including a non-transitory computer readable storage medium in which computer program instructions are stored, which instructions, when executed by a computer, cause the computer to perform the steps of:
   focusing cameras on at least one point of an object in the volume;
   transmitting UV light and sterilant into the volume;
   scanning, using the cameras, the at least one point of the object and determining an amount of absorbance at the at least one point;
   calculating, from said determined amount of absorbance, a concentration of the sterilant for each of the at least one points; and
   when the concentration is greater than a threshold, removing the sterilant from the volume.

16. The computer software product according to claim 15, the scanning further comprising partitioning the chamber into a grid of voxels and scanning the voxels.

17. The computer software product according to claim 15, the calculating being performed by measuring the amount of absorbance at the at least one point.

18. The computer software product according to claim 15, wherein the amount of absorbance is proportional to the concentration of the sterilant.

19. The computer software product according to claim 15, wherein the cameras are stereoscopic cameras.

20. The computer software product according to claim 15, wherein the threshold is 630 mg/L.

* * * * *